US012560523B2

(12) United States Patent
Wang et al.

(10) Patent No.:    US 12,560,523 B2
(45) Date of Patent:       Feb. 24, 2026

(54) DATA ACQUISITION AND ANALYSIS METHOD BASED ON DIABETES DATA ANALYSIS AND PROCESSING EQUIPMENT

(71) Applicant: Air Force Medical University, Shaanxi (CN)

(72) Inventors: Yayun Wang, Shaanxi (CN); Yanling Yang, Shaanxi (CN); Ze Li, Shaanxi (CN); Feifei Wu, Shaanxi (CN); Xiaodong Li, Shaanxi (CN); Jinghao Chen, Shaanxi (CN); Yunhu Bai, Shaanxi (CN)

(73) Assignee: Air Force Medical University, Xi'an (CN)

( * ) Notice: Subject to any disclaimer, the term of this patent is extended or adjusted under 35 U.S.C. 154(b) by 546 days.

(21) Appl. No.: 18/317,941

(22) Filed:      May 16, 2023

(65) Prior Publication Data

US 2024/0280462 A1      Aug. 22, 2024

(30) Foreign Application Priority Data

Feb. 21, 2023    (CN) .......................... 202310143662.3

(51) Int. Cl.
| | | |
|---|---|---|
| *G01N 15/1404* | (2024.01) | |
| *G01N 15/1429* | (2024.01) | |
| *G01N 33/49* | (2006.01) | |

(52) U.S. Cl.
CPC ..... *G01N 15/1404* (2013.01); *G01N 15/1429* (2013.01); *G01N 33/4915* (2013.01); *G01N 2015/1418* (2013.01); *G01N 2800/042* (2013.01)

(58) Field of Classification Search
CPC .......... G01N 15/1404; G01N 15/1429; G01N 33/4915; G01N 2015/1418; G01N 2800/042; G01N 2015/016; G01N 2015/1402; G01N 15/1459; G01N 2015/1006; G01N 15/14; A61B 5/103; Y02A 50/30
See application file for complete search history.

(56) References Cited

U.S. PATENT DOCUMENTS

| | | | | |
|---|---|---|---|---|
| 2005/0009060 A1* | 1/2005 | Beernink | ............. | G01N 33/582 |
| | | | | 435/40.5 |
| 2014/0147860 A1* | 5/2014 | Kaduchak | ........ | G01N 33/56966 |
| | | | | 435/7.21 |
| 2019/0360910 A1* | 11/2019 | Tsuji | ...................... | G01N 15/14 |

\* cited by examiner

*Primary Examiner* — Jennifer Wecker
*Assistant Examiner* — Britney N. Washington

(57)                ABSTRACT

The present disclosure discloses a data acquisition and analysis method based on diabetes data analysis and processing equipment, and relates to the field of diabetes data analysis and prediction. The equipment includes a computer, a placement rack and a flow cytometer. The mitochondrial membrane potential data in the neutrophil is performed independent evaluation and analysis. If the proportion of cells with increased mitochondrial membrane potential are in the neutrophil is greater than 70%, the person is at the risk of diabetes, otherwise the risk is lower, so that the subsequent development of diabetes in a person with normal blood glucose can be predicted, and the diabetes can be prevented in advance.

8 Claims, No Drawings

DATA ACQUISITION AND ANALYSIS METHOD BASED ON DIABETES DATA ANALYSIS AND PROCESSING EQUIPMENT

TECHNICAL FIELD

The present disclosure relates to the technical field of diabetes data analysis and prediction, in particular to a data acquisition and analysis method based on diabetes data analysis and processing equipment.

BACKGROUND TECHNOLOGY

Diabetes is a group of metabolic diseases characterized by hyperglycemia. Hyperglycemia is caused by insulin secretion defect or impaired biological action, or both. Long-term hyperglycemia will impair various tissues, especially chronic damage and dysfunction of eyes, kidneys, heart, blood vessels and nerves.

Generally, in testing diabetes, whether the patients with diabetes are judged through the fasting blood glucose content; however, this method can only test for diabetics, it is difficult for the people with normal blood glucose to acquire their mitochondrial membrane potential effectively; thereby a data acquisition and analysis method based on diabetes data analysis and processing equipment is needed.

SUMMARY OF THE PRESENT DISCLOSURE

An objective of the present disclosure is to solve the problem that it is difficult for the person with normal blood glucose to acquire, analyze and judge their own blood glucose data in the prior art, so that a data acquisition and analysis method based on diabetes data analysis and processing equipment is provided.

In order to achieve the above objective, the following technical solutions are adopted in the present disclosure:

a data acquisition and analysis method based on diabetes data analysis and processing equipment. The equipment includes a computer, a placement rack and a flow cytometer; wherein the flow cytometer is mounted on the placement rack; the computer is mounted on the placement rack; and the steps of the data acquisition method are as follows:

step 1: cells acquisition: the white blood cells of the peripheral venous blood of the patient are first acquired; the red blood cells are removed; then the peripheral venous blood cell suspension is added into an anticoagulant centrifuge tube to be centrifuged; and the supernatant after centrifugation is removed;

step 2: cells processing: PBS solution is added to the liquid after preliminary processing in step 1 for washing and the washed liquid is centrifuged again; and then the supernatant after centrifugation is removed;

step 3: cells reprocessing: the unit number of the white blood cells in the liquid after processing in step 2 is adjusted artificially; a probe is loaded in the adjusted liquid; and finally the cells are washed with serum-free culture solution;

step 4: flow cytometer test: the cells are added to the flow cytometer, by which, the mitochondrial membrane potential in the white blood cells is tested;

step 5: independent evaluation and analysis of the neutrophil data are performed in the process of test; and step 6: if the proportion of cells with increased mitochondrial membrane potential are in the neutrophil is greater than 70%, the person is at higher risk of diabetes; and if the proportion of cells with increased mitochondrial membrane potential are in the neutrophil is less than 70%, the person is at lower risk of diabetes.

The duration of centrifugation is 4-8 min and the rotational speed of centrifugation is 1,000 rpm during cells acquisition.

The duration of centrifugation is 5-9 min and the rotational speed of centrifugation is 1,000 rpm during cells processing.

The duration of centrifugation is 5-9 min and the rotational speed of centrifugation is 1,000 rpm during cells processing.

The flow cytometer needs to be cleaned and preheated before the flow cyto meter is operated.

Compared with the prior art, the present disclosure has the following beneficial effects:

according to the present disclosure, the white blood cells in the peripheral venous blood are first acquired, and the cells are put into the flow cytometer. The flow cytometer is set to a voltage of 433 mV for the PE channel and 485 mV for the FITC. The mitochondrial membrane potential in the white blood cells is tested by the flow cytometer, so that the mitochondrial membrane potential of the tested person can be analyzed comprehensively, which is conducive to analyzing and judging the blood glucose data of the person with normal blood glucose.

SPECIFIC EMBODIMENTS

Example 1

Step 1, the white blood cells in peripheral venous blood of the patient are first acquired, and the red blood cells are removed; then the peripheral venous blood cell suspension is added into an anticoagulant centrifuge tube to be centrifuged; then the supernatant after centrifugation is removed; PBS solution is added to the liquid after preliminary processing in step 1 for washing and the washed liquid is centrifuged again; the supernatant after centrifugation is removed; and the centrifugation duration is 4-8 min and the rotational speed of centrifugation is 1,000 rpm during cells acquisition;

step 2, the unit number of the white blood cells in the liquid after processing in step 1 is adjusted artificially; a probe is loaded in the adjusted liquid; the cells are incubated in a cell incubator with the mitochondrial membrane potential test probe JC-1 for 20 min at the temperature of 37°; and finally the cells are washed with serum-free culture solution;

step 3, the cells are put into the flow cytometer. The flow cytometer is set to a voltage of 433 mV for the PE channel and 485 mV for the FITC; and the mitochondrial membrane potential in the white blood cells is tested by the flow cytometer; and step 4, independent evaluation and analysis are performed on the neutrophil data in the process of testing; if the proportion of cells with increased mitochondrial membrane potential are in the neutrophil is greater than 70%, the person is at higher risk of diabetes; and if the proportion of cells with increased mitochondrial membrane potential are in the neutrophil is less than 70%, the person is at lower risk of diabetes.

Based on the above example, 100 people are tested. The number of people with the mitochondrial membrane potential proportion less than 5% is 21, and the number of people with the mitochondrial membrane potential proportion greater than 5% is 89. 6 of the 100 people with confirmed diabetes are in the group with mitochondrial membrane potential proportion less than 5%, and 14 people of the remaining 15 people with mitochondrial membrane potential proportion less than 5% have fasting glucose increase after six months.

Example 2

Step 1, a blood glucose test is first performed on 100 people, and the test is performed twice, once on a fasting basis and another in 2 hours after a meal; and Step 2, the results of the test are counted.

Based on the above-mentioned example, 100 people are tested. The number of people whose fasting blood sugar exceeds 7 and whose blood sugar exceeds 11.1 two hours after meal is 13. And then the number of people whose fasting blood sugar is 6.5-7 and whose blood sugar exceeds 10.6-11.1 two hours after meal is counted, and the counted number is 24. Another test is performed after six months, in this test results, among the 24 people, the total number of people with increased fasting blood glucose and two-hour blood glucose after meal is 15.

The above mentioned are only better embodiments of the present disclosure, but the scope of protection of the present disclosure is not limited to them. Within the technical scope disclosed by the present disclosure, any modifications or replacements made by any skilled familiar with the technical field of the present disclosure are covered by the scope of protection of the present disclosure.

What is claimed is:

1. A data acquisition and analysis method based on diabetes data analysis and processing equipment; the equipment comprises a computer, a placement rack and a flow cytometer, wherein the flow cytometer is mounted on the placement rack, and the computer is mounted on the placement rack; and characterized in that the data acquisition method comprises the following steps:

step 1: cells acquisition: the white blood cells in peripheral venous blood of the patient are first acquired; the red blood cells are removed; then the peripheral venous blood cell suspension is added into an anticoagulant centrifuge tube to be centrifuged; and the supernatant after centrifugation is removed;

step 2: cells processing: PBS solution is added to the liquid after preliminary processing in step 1 for washing and the washed liquid is centrifuged again; and then the supernatant after centrifugation is removed;

step 3: cells reprocessing: the unit number of the white blood cells in the liquid after processing in step 2 is adjusted artificially; a probe is loaded in the adjusted liquid; and finally the cells are washed with serum-free culture solution;

step 4: flow cytometer test: the cells are added to the flow cytometer, by which, the mitochondrial membrane potential in the white blood cells is tested; and step 5: independent evaluation and analysis of the neutrophil data are performed in the process of test.

2. The data acquisition and analysis method based on diabetes data analysis and processing equipment according to claim 1, characterized in that, the loaded probe is the mitochondrial membrane potential test probe JC-1.

3. The data acquisition and analysis method based on diabetes data analysis and processing equipment according to claim 2, characterized in that, the cells are incubated in a cell incubator for 20 min at the temperature of 37° with the mitochondrial membrane potential test JC-1 before the cells are washed with serum-free culture solution.

4. The data acquisition and analysis method based on diabetes data analysis and processing equipment according to claim 1, characterized in that, the flow cytometer is set to a voltage of 433 mV for the PE channel and 485 mV for the FITC.

5. The data acquisition and analysis method based on diabetes data analysis and processing equipment according to claim 1, characterized in that, the duration of the centrifugation is 4-8 min and the rotational speed of centrifugation is 1,000 rpm during cell acquisition.

6. The data acquisition and analysis method based on diabetes data analysis and processing equipment according to claim 1, characterized in that, the flow cytometer is set to a voltage of 433 mV for the PE channel and 485 mV for the FITC.

7. The data acquisition and analysis method based on diabetes data analysis and processing equipment according to claim 1, characterized in that, the duration of centrifugation is 5-9 min and the rotational speed of centrifugation is 1,000 rpm during cells processing.

8. The data acquisition and analysis method based on diabetes data analysis and processing equipment according to claim 1, characterized in that, the flow cytometer needs to be cleaned and preheated before the flow cytometer is operated.

* * * * *